(12) United States Patent
Zhang et al.

(10) Patent No.: US 7,368,280 B2
(45) Date of Patent: May 6, 2008

(54) DETECTION OF BIOSPECIFIC INTERACTIONS USING AMPLIFIED DIFFERENTIAL TIME DOMAIN SPECTROSCOPY SIGNAL

(75) Inventors: Xi-Cheng Zhang, Melrose, NY (US); Samuel Peter Mickan, Burnside (AU); Abdellah Menikh, Toronto (CA)

(73) Assignee: Rensselaer Polytechnic Institute, Troy, NY (US)

( * ) Notice: Subject to any disclaimer, the term of this patent is extended or adjusted under 35 U.S.C. 154(b) by 437 days.

(21) Appl. No.: 10/515,607

(22) PCT Filed: May 22, 2003

(86) PCT No.: PCT/US03/16122

§ 371 (c)(1),
(2), (4) Date: Nov. 23, 2004

(87) PCT Pub. No.: WO03/100396

PCT Pub. Date: Dec. 4, 2003

(65) Prior Publication Data

US 2006/0045807 A1 Mar. 2, 2006

Related U.S. Application Data

(60) Provisional application No. 60/382,761, filed on May 23, 2002.

(51) Int. Cl.
*C12M 1/34* (2006.01)
*C12M 3/00* (2006.01)

(52) U.S. Cl. ............... 435/287.2; 435/283.1; 435/288.3; 435/288.7; 435/287.1; 422/50; 422/61; 422/68.1; 436/518; 436/528; 436/529; 436/524; 436/525

(58) Field of Classification Search ............. 435/283.1, 435/288.3, 288.7, 287.2, 287.1; 422/50, 422/61, 68.1; 436/518, 528, 529, 524, 525
See application file for complete search history.

(56) References Cited

U.S. PATENT DOCUMENTS 4,036,946 A 7/1977 Kleinerman (Continued)

FOREIGN PATENT DOCUMENTS

GB 2 136 953 A 9/1984

OTHER PUBLICATIONS

Brucherseifer et al., Label-free probing of the binding state of DNA by time-domain terahertz sensing, 2000, Applied Physics Letters, vol. 77, No. 24, pp. 4049-5051.*

(Continued)

*Primary Examiner*—Long V. Le
*Assistant Examiner*—Melanie J. Yu
(74) *Attorney, Agent, or Firm*—RatnerPrestia

(57) ABSTRACT

A method for detecting specific associations between a tethered molecule and an untethered target molecule. The method comprises (1) selecting a tethered molecule; (2) alternately impinging THz radiation onto the tethered molecule and onto a sample including the tethered and untethered target molecules; (3) detecting the radiation impinged on the tethered molecule to form a reference signal and the radiation impinged on the sample to form a sample signal; and (4) comparing the reference signal with the sample signal to generate a specimen signal indicative of an association between the selected tethered and target molecules. The method will detect whether a selected tethered molecule and the desired target exhibit any affinity or, in cases where the affinity is known, will detect the presence of the target molecule in a sample. Also provided is an apparatus for detecting specific associations between a tethered molecule and an untethered target molecule.

12 Claims, 6 Drawing Sheets

U.S. PATENT DOCUMENTS

| | | | |
|---|---|---|---|
| 5,671,303 A | 9/1997 | Shieh et al. | |
| 6,057,928 A * | 5/2000 | Li et al. | 356/445 |
| 6,388,799 B1 * | 5/2002 | Arnone et al. | 359/326 |
| 6,430,513 B1 * | 8/2002 | Wang et al. | 702/28 |
| 6,650,357 B1 * | 11/2003 | Richardson | 348/80 |
| 6,665,075 B2 * | 12/2003 | Mittleman et al. | 356/450 |
| 6,723,991 B1 * | 4/2004 | Sucha et al. | 250/341.1 |
| 6,777,181 B2 * | 8/2004 | Matsumoto | 435/6 |
| 6,917,428 B2 * | 7/2005 | Zhu | 356/369 |
| 6,986,739 B2 * | 1/2006 | Warren et al. | 600/159 |
| 7,148,010 B2 * | 12/2006 | Nagel et al. | 435/6 |
| 2001/0009774 A1 * | 7/2001 | Shin et al. | 436/518 |
| 2002/0067480 A1 * | 6/2002 | Takahashi | 356/317 |
| 2002/0118371 A1 * | 8/2002 | Jiang et al. | 356/517 |

OTHER PUBLICATIONS

Mickan et al., Amplification and modeling of bioaffinity detection with terahertz spectroscopy, Biomedical Applications of Micro- and Nanoengineering, Proceedings of SPIE, vol. 4937 (2002) pp. 334-342.

International Search Report for PCT International Application No. PCT/US 03/16122, mailed Oct. 30, 2003.

* cited by examiner

DETECTION OF BIOSPECIFIC INTERACTIONS USING AMPLIFIED DIFFERENTIAL TIME DOMAIN SPECTROSCOPY SIGNAL

This application is a U.S. National Phase Application of PCT International Application PCT/US 03/16122 filed May 22, 2003 which claims priority to U.S. Provisional Application 60/382,761 filed May 23, 2002.

FIELD OF THE INVENTION

This invention relates to bioanalytical technology and, more particularly, to a method and associated apparatus for detecting the affinity between a ligand and a biological specimen and using the detected affinity in a bioassay application.

BACKGROUND OF THE INVENTION

The accurate detection of minute amounts of chemical and biological substances has been a major goal in bioanalytical technology throughout the twentieth century. Over the years, a wide variety of biosensing strategies have been developed to satisfy numerous needs. The general aim is to develop a scheme that is able to simplify sample preparation steps, provide high selectivity and sensitivity, respond in a continuous and reversible manner, and accomplish measurements without sample perturbation. Added to these conditions are other goals of convenience such as reusability, portability, low costs for mass production, miniaturization, and ease of use. These features are the most demanding parameters for biosensor designs.

The use of fluorescent indicators in bioassays has met with a certain level of success. Many biological molecules show an inherent fluorescence (associated with the amino acid derivatives of tryptophan or tyrosine, nucleic acids, or other metabolites such as porphyrins). Exploiting this inherent property for bioassay is not a simple procedure, however, because the emitted fluorescence signal is generally weak and often difficult to distinguish above a background signal. To overcome these limitations, an additional step of adding fluorescent labels has been used to mark the desired specimen for easier detection. Such addition disturbs the sample, however, and requires extra steps in sample preparation. Other limitations of fluorescence indicators include fluorescence quenching by other solutes and the insensitivity of fluorescence to certain binding events. In current solid-phase immunoassay procedures, wash steps are labor intensive and time consuming when performed manually and would require complicated and, therefore, expensive robotics in an automated format.

Recently, THz-TDS (Terahertz time domain spectroscopy) has emerged as a successful method to probe the electrical properties of thin solid films in the spectral interval from 0.1 to 10 THz, between the infrared and microwave bands. This technique provides a new alternative to measure the refractive index of thin solid films without sample perturbation. The heart of the THz system is a mode-locked Ti:sapphire femtosecond (fs) laser, which generates fs duration pulses at a MHz repetition rate and low average power. A beam splitter separates the laser beam into excitation and reference pulses. The excitation pulse illuminates an unbiased GaAs semiconductor emitter wafer to generate a THz beam, which is collimated and focused onto an electro-optic sampling crystal, <110> oriented ZnTe, with parabolic mirrors. A pellicle after the second parabolic mirror allows the reference beam to travel collinearly with the THz wave across the electro-optic crystal. A quarter wave plate (QWP), a Wollaston prism (P), and a pair of photodiodes are assembled for the balanced detection of the THz beam.

Unfortunately, compared to the existing biosensors in the marketplace, current THz-based systems suffer from poor signal-to-noise ratios and sensitivity. The most useful techniques for monitoring on-off binding in the far-infrared are attenuated total internal reflection Fourier transform infrared (ATR-FTIR) spectroscopy and Raman spectroscopy. Unfortunately, the complications associated with cryogenic detectors in FTIR and Raleigh lines in Raman are among the anomalies that hamper FTIR and Raman spectroscopy from being widely used. Also, in general, FTIR has a relative poor signal-to-noise ratio for frequencies less than 1 THz.

Therefore, a need remains for a new non-invasive biosensor technology having application, for example, in health care, food monitoring, and weapon detection.

SUMMARY OF THE INVENTION

To meet this and other needs, and in view of its purposes, the present invention provides a method for detecting specific associations between a tethered molecule and an untethered target molecule. The method comprises the following steps:

1) selecting a molecule to serve as the tethered molecule;
2) alternately impinging THz radiation onto the tethered molecule and onto a sample including the tethered molecule and the untethered target molecule;
3) detecting the radiation impinged on the tethered molecule to form a reference signal and the radiation impinged on the sample including the tethered and target molecules to form a sample signal; and
4) comparing the reference signal with the sample signal to generate a specimen signal indicative of an association between the selected tethered and target molecules.

The method may be used to detect whether a selected tethered molecule and the desired target exhibit any affinity, or, in cases where the affinity is known, to detect the presence of the target molecule in a sample.

In typical biosensing applications, the detected association comprises biomolecular interactions selected from the group consisting of covalent bonds, hybridization, hydrogen-bonding interactions, hydrophilic interactions, and specific non-covalent binding interactions. The tethered and target molecules are selected from the group consisting of ligands receptors, antigens, antibodies, DNA, and RNA.

In a preferred embodiment of the invention, the target is bound onto a signal amplifying medium, such as agarose, gold, or carbon. In a particular embodiment comprising a ligand, the ligand is biotin and the target receptor is avidin, preferably avidin attached to agarose beads.

Still within the scope of the invention there is provided an apparatus for detecting specific associations between a tethered molecule and an untethered target molecule, the apparatus comprising:

a. a THz radiation source emitting a pulsed THz radiation beam along a THz radiation beam path;
b. a source of a pulsed optical radiation probe beam traveling along an optical radiation path;
c. a THz radiation detector located in the THz radiation beam path and in the optical radiation path whereby the THz radiation beam modulates the optical radiation beam to form a modulated optical radiation beam traveling along a modulated optical beam path;

d. a modulated optical beam detector in the modulated beam path for generating an electronic signal indicative of the modulation of the optical beam;

e. a sample holder in the THz radiation beam path ahead of the THz radiation detector, the sample holder adapted to hold and to movably position in the radiation beam path alternately a first and a second sample, the first sample comprising the tethered molecule and selected to provide a reference signal and the second sample containing a combination of the tethered molecule and the target; and f. electronic signal processing circuitry for comparing detection signals when the first sample is placed in the THz radiation path with detection signals when the second sample is in the THz radiation path.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 5A is an enlarged elevation view of a galvanometric arrangement for mounting a sample for detection in accordance with the present invention;

FIG. 5B is a schematic representation of the sample location relative to the THz beam in accordance with the present invention.

DETAILED DESCRIPTION OF THE INVENTION

Terahertz (THz) time-domain spectroscopy operates in the radiation domain between the electronic band (i.e., microwaves) and the photonic band (i.e., infrared), and provides for sensitive measurement of changes in the indices of refraction of materials. The sensitivity of this technique can be exploited to detect and measure molecular interactions.

The present invention provides a method of probing biomolecular interactions using THz radiation. The biomolecular interactions that may be detected include non-covalent and covalent molecular interactions such as ligand and receptor binding, antigen and antibody binding, and DNA and RNA hybridization interactions. Specific interactions that may be examined include enzyme and coenzyme binding, as well as cell surface binding to cell-specific signaling agents. Generally, the method of the present invention allows for detecting specific associations between a tethered molecule and an untethered target molecule.

Figure 1:
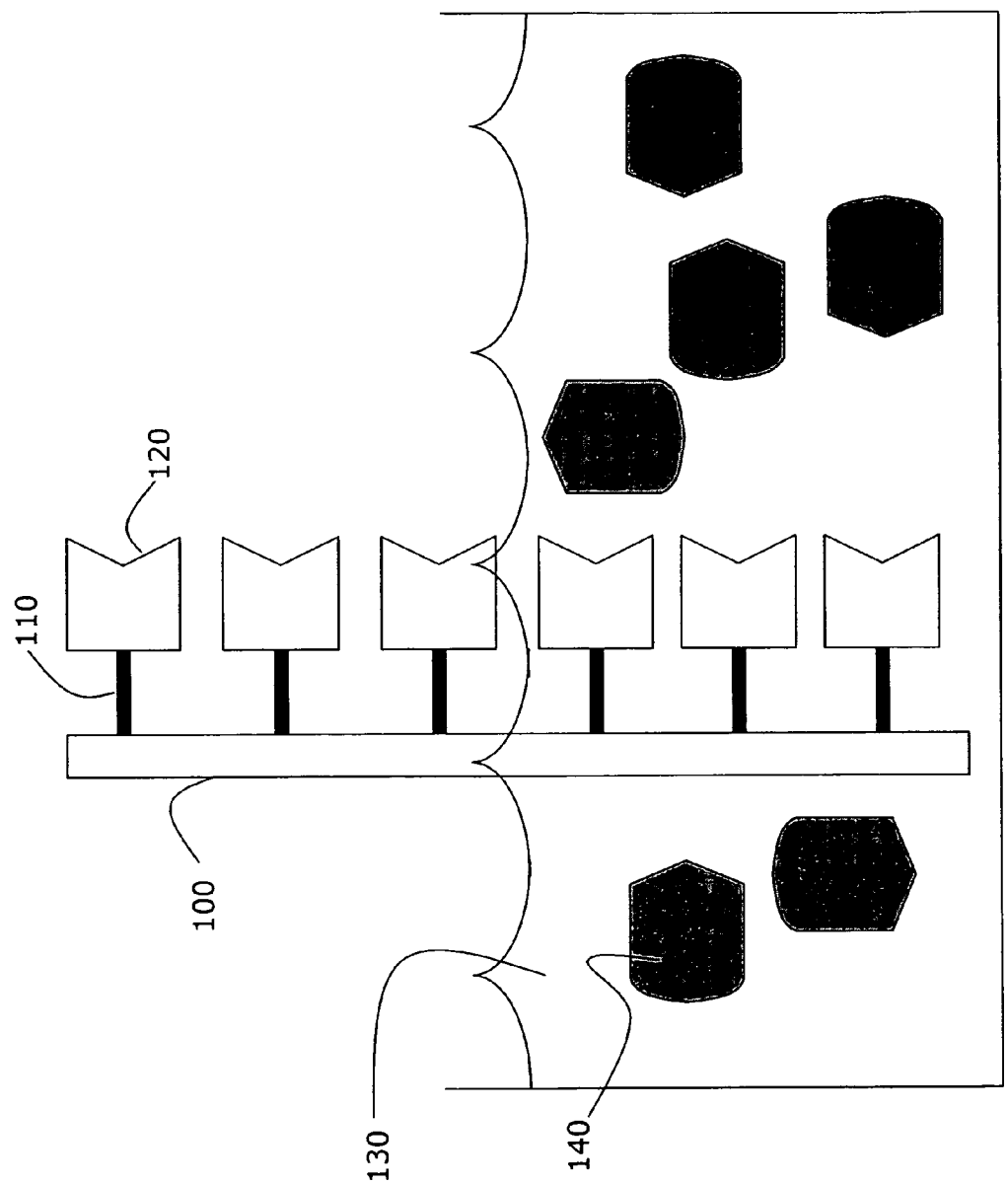
FIG. 1 is a schematic representation of a glass slide with tethered molecules, as it is partially exposed to untethered target molecules.

A sample for detection may be prepared by tethering a molecule to a support, such as a glass slide, as shown in FIG. 1. A support 100 may be treated with binding material 110 if necessary. Binders include molecules or treatments that improve the tether between the support 100 and the tethered molecule 120. Tethered molecules 120 are attached to the support 100. A portion of the support 100 is then exposed to target molecules 140. As shown in FIG. 1, approximately half of the surface area of the support 100 is exposed to a solution 130 containing target molecules 140. Depending on the binding affinity between the tethered and target molecules 120, 140, respectively, and the concentration of molecules on the support 100 and in the solution 130, an interaction may form between the tethered molecule 120 and the target molecule 140.

Figure 2:
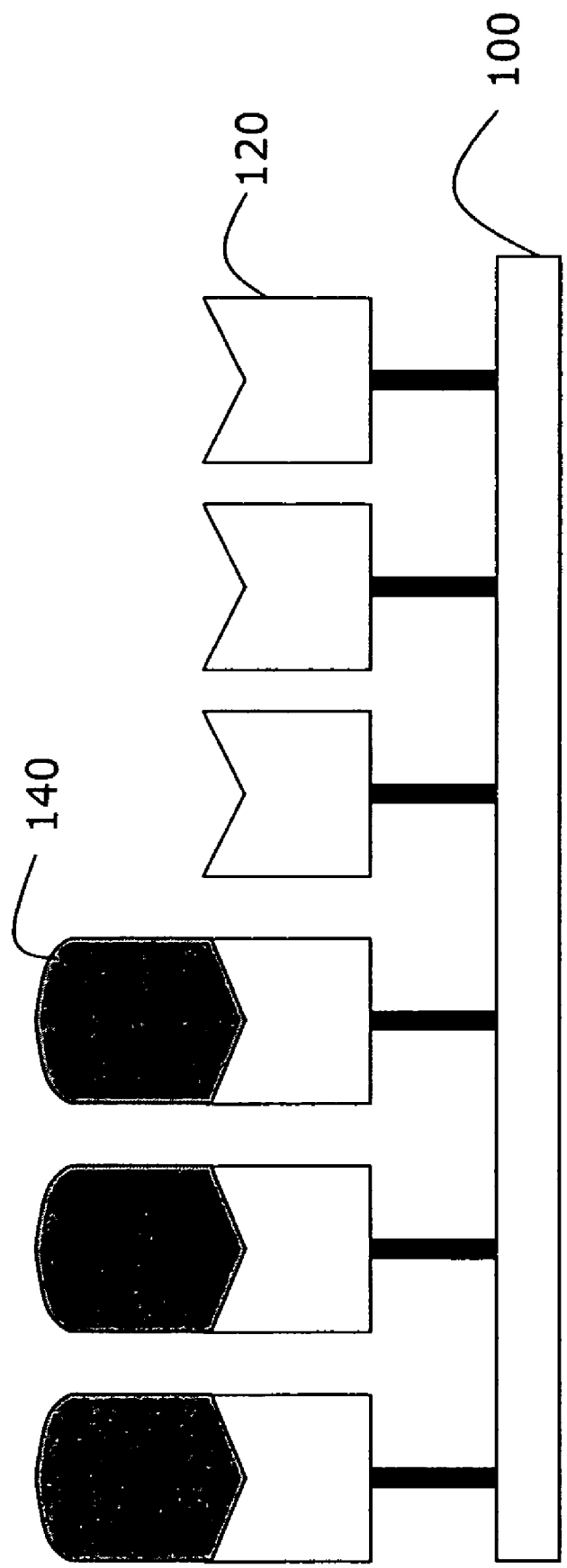
FIG. 2 is a schematic of a prepared sample with receptors only and receptors bound by specific ligands.

FIG. 2 shows a schematic of the support 100 of FIG. 1 after being exposed to the target molecule solution 130. The portion of the support 100 that was exposed to the solution 130 has target molecules 140 bound to the tethered molecules 120. A difference measurement using time domain THz spectroscopy involves subtracting the detected signal provided by the unexposed portion of the support 100 (i.e., the reference signal) from the detected signal provided by the exposed portion of the support 100 (i.e., the target signal).

By measuring the difference between a reference signal and a target signal, greater sensitivity is achieved. Specifically, differential time domain THz spectroscopy can measure very slight changes in index of refraction at a molecular boundary. The change in index of refraction induced upon forming a molecular interaction can be exaggerated by attaching a refracting body onto the target molecule.

Figure 3:
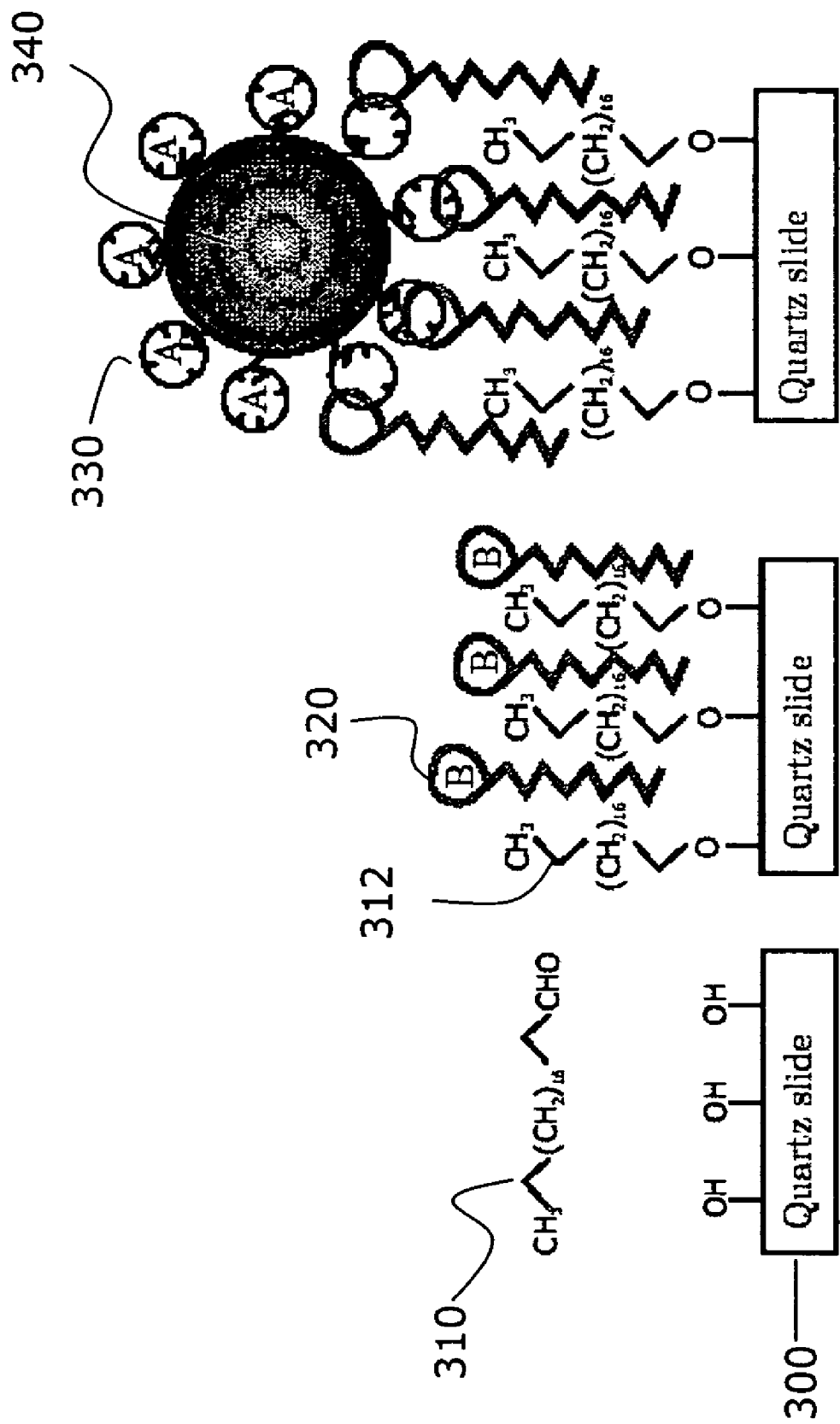
FIG. 3 is a schematic of an exemplary quartz slide prepared according to the present invention.

An example of attaching an additional refracting body onto the target molecule is shown in FIG. 3. and discussed in detail in Example 3 below. As shown in FIG. 3, a quartz slide 300 is treated with nitric acid and exposed to octadecanol solution 310. The octadecanol binds to the treated quartz slide and serves as a binding agent 312 to secure tethered molecules 320 to the quartz slide 300. As shown in FIG. 3, the binding agent 312 is covalently bound to the quartz slide 300 (i.e., the support) while the tethered molecule 320 is non-covalently secured to the binding agent 312 through hydrophobic interactions. In the present invention, the tethered molecule may be secured to the support via covalent or non-covalent interactions, such as hydrogen bonding and hydrophilic or hydrophobic interactions. In addition, an intermediary agent, such as the octadecanol in FIG. 3, may be used to facilitate the association between the tethered molecule and the support.

Once the tethered molecule is associated with a support, a portion of the support is exposed to the target molecule. The target molecule 330 of FIG. 3 is shown attached to an additional refracting body 340. The additional refracting body 340 is an amplifying medium and may be a biological molecule, such as a protein, a synthetic molecule, or an inorganic ion. Gold or carbon microspheres may be used to provide even greater enhancement of the difference signal. Depending on the target molecule, silica beads may also be used to amplify the difference signal between the reference and specimen portions of the sample.

As shown in FIG. 3, several target molecules 330 are bound to the additional refracting body 340. This serves to exaggerate the difference in the index of refraction as compared to the target molecule alone, as described in more detail in Example 2. The additional refracting body 340 may be an agarose bead.

The present invention includes tethering a known molecule to a sample surface and exposing a portion of the slide or support to a collection of target molecules to assess whether the target molecules have a specific interaction with the tethered molecule. This embodiment of the invention may be useful in assaying molecules for potential drug targets. Because the present invention does not require any labeling or modification of the molecules, it does not suffer from the difficulties associated with traditional, invasive detection methods.

The present invention also includes detecting and purifying genetic material. By tethering DNA or RNA molecules to a surface, the present invention allows facile detection of the corresponding DNA or RNA molecule in a target solution. Other applications include determining the presence of a target molecule. An embodiment of the present invention may allow detection of small amounts of contaminants in water or food. Similarly, blood samples may be tested for the presence of disease-indicating agents.

EXAMPLES

The following examples are included to more clearly demonstrate the overall nature of the invention. These examples are exemplary, not restrictive, of the invention.

Example 1

In an example of the present invention, the binding between the eggwhite glycoprotein, avidin, and vitamin H, biotin was detected by differential time domain THz spectroscopy. Avidin is a known protein characterized by its four identical binding sites for biotin. In this example, biotin is the tethered molecule, and is non-covalently attached to the support surface.

Prior to biotin deposition, the quartz slides were cleaned in 50% hot nitric acid for an hour, and then rinsed thoroughly in double distilled water. The quartz slides were further subjected to 1 mg/ml octadecanol solution for half an hour. The hydrophobic substrate was immobilized on the hydrophilic surface through molecular self-assembly. The spontaneous organization of the biotin lipid into the octadecanol self-assembled bilayers provides a certain level of stability to the octadecanol-biotin complexes.

After drying and washing the octadecanol-treated slides with double distilled water, the sample was dipped in a solution of 0.5 mg/ml biotin dissolved in chloroform/methanol (5:1), and allowed to incubate for 45 minutes. Immersion in the biotin solution resulted in an increase in sample thickness of 5 nm/cm$^2$. The increase in thickness was generated by the biotin associating with octadecanol through hydrophobic interaction. Lastly, to eliminate the effects of non-specific interactions, the quartz slides were further incubated in 1% bovine serum albumin, then dried and washed several times with phosphate buffer solution. The slide was then exposed to target molecules on one side. A portion of the slide was exposed to a solution of 10.3 ng of avidin in 200 µl double-distilled water. Approximately 1 cm$^2$ of the biotin prepared slide was exposed, and allowed to incubate for half an hour in the avidin solution. After drying, the exposed slide was washed with double-distilled water to remove unbound molecules. The only avidin remaining formed a thin layer of tightly bound biotin-avidin complexes.

The slide as prepared included a reference sample portion (biotin only) and a specimen sample portion (biotin-avidin). In collecting the differential time-domain THz spectra, the slide was rapidly oscillated so that the THz rays alternately passed through the reference sample portion and the specimen sample portion. By scanning both portions of the prepared slide, a measurable difference signal was generated. This signal is graphed as a dotted line 410 in FIG. 4 and is directly proportional to the difference signals between the unbound biotin and the avidin-bound biotin complexes.

Figure 4:
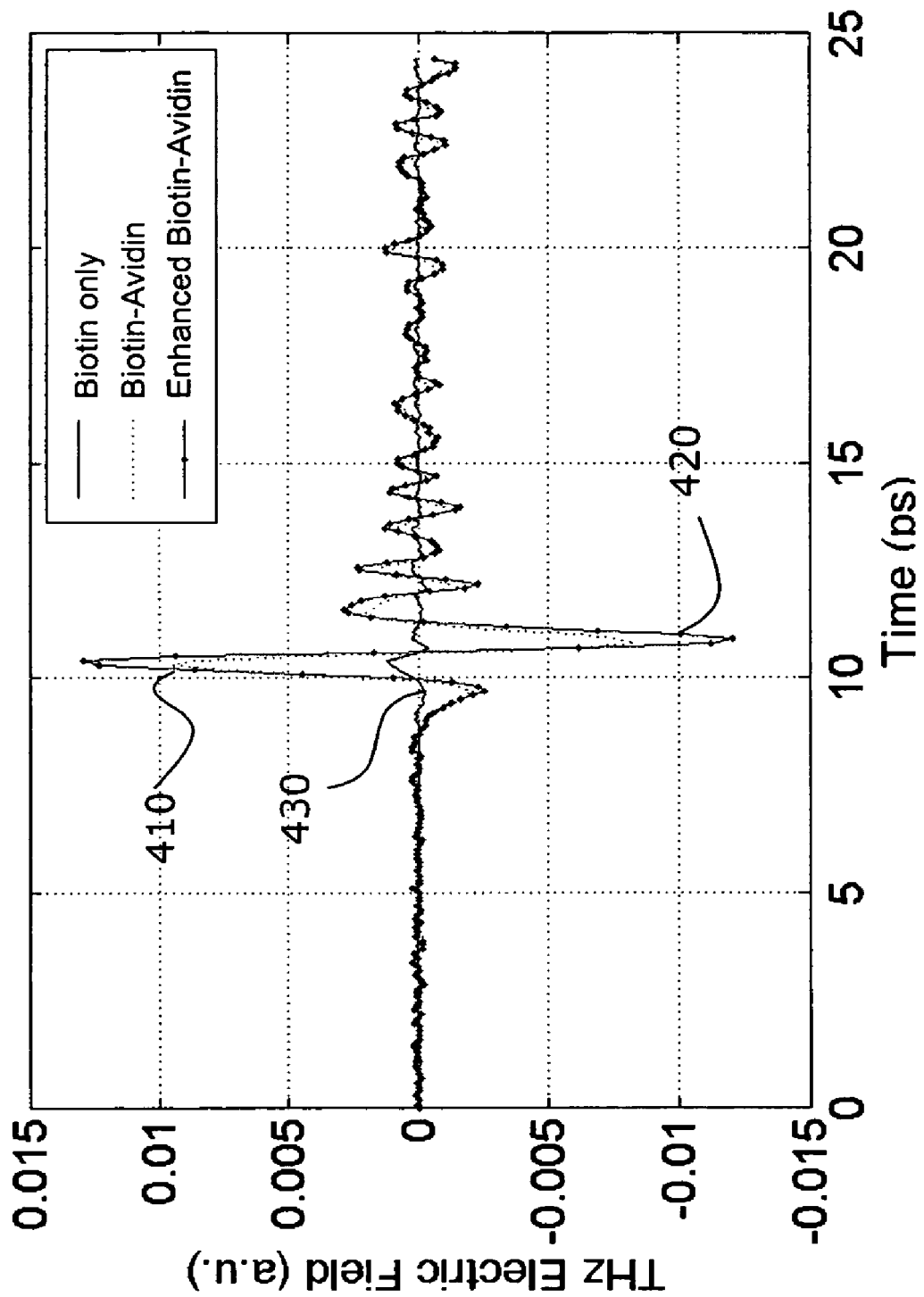
FIG. 4 is a graph of the time domain THz pulses obtained according to the present invention.

As shown in FIG. 4, a small measurable signal exists for the experimental control 430. The control signal was generated by sampling separate portions of a biotin-only slide. The small difference signal is believed to be due to biotin surface inhomogeneity, instrument noise, or both.

Example 2

Similar results were achieved by securing avidin to the slide surface and exposing a portion of the avidin-treated slide to a solution of biotin. In this case, avidin was the tethered molecule, and was covalently attached to a glass slide. The procedure for covalent immobilization of avidin on glass slides included treating the surface of the glass slides with thiol-terminal silanes and a succinimde crosslinker. This treatment increased the density of bound avidin on the glass slides. See also S. Mickan, A. Menikh, J. Munch, D. Abbott & X.-C. Zhang, "Amplification and modeling of bioaffinity detection with terahertz spectroscopy," Proceedings of SPIE—Biomedical Applications of Micro- and Nanoengineering, SPIE Vol. 4937, pp. 334-42 (Dan Nicolau ed., Melbourne, Australia, Dec. 16-18, 2002), the contents of which are incorporated in this document by reference.

In preparing the sample slide, the glass slides were cleaned, silanized, and crosslinked prior to deposition of the avidin film. Two glass microscope slides, each approximately 0.96 mm thick, were prepared simultaneously, one as the test sample and the second as a reference. The glass substrates were cleaned with 50% hot nitric acid, then rinsed several times with doubly distilled water. The substrate was placed in a 5% solution of 3-mercaptopropyltrimethoxysilane in toluene for 1 hour. The organic cross linker succinimide ester was dissolved in dimethylformide to a final concentration of 3 mM. The silanized substrate was treated with the cross linker for another hour, washed thoroughly in phosphate-buffered saline (PBS), and dried under vacuum.

To tether the avidin to the slides, 2 mg of avidin were dissolved in 10 ml of sodium phosphate buffer, pH 7.4. An aliquot of 200 µl solution was applied to each glass slide, and incubated for about 30 minutes, producing a film surface area of approximately 15 by 30 mm. After washing and drying under nitrogen, half of the biosensor slide was exposed to 10 µl of a solution containing 10 µg m$^{-1}$ of biotin, dissolved in chloroform and methanol mixed in the ratio of five to one. The resulting concentration of biotin was 0.1 µg cm$^{-2}$. Avidin is a very stable protein, and the avidin-biotin complex is known to retain its activity even in strong denaturants. The ensemble was washed with a mixture of PBS to remove unbound molecules.

The reference slide of pure avidin was not exposed to the biotin solution. Washing the slide removed any material that was weakly bound to the avidin layer. The biosensor film thickness was estimated to be approximately 1 µm, which corresponds to many layers of the protein avidin. The thickness of the biotin layer was approximately 40 nm, as measured with an atomic force microscope (AFM). The topographical roughness of avidin film both with and without biotin, measured on the AFM, was of the same order of magnitude and randomly distributed across the surface with a quasi-period of about 30 µm. When measured with differential-time-domain spectroscopy (DTDS), the signal was a spatial average of the spot size of the focused THz-radiation beam, which had a 1 mm diameter (FWHM). The random roughness of the film was largely averaged out over the THz-radiation spot, while the consistent contribution of the biotin in half of the biosensor generated a discernable signal.

The data were collected on the THz apparatus as described in this document. The femtosecond laser source generated 150 fs pulses at 86 MHz and 1.5 W of average power. The pump beam was 700 mW after the optical modulator, and the THz-radiation was generated in an unbiased GaAs wafer. The THz-radiation detector was a 2 mm thick crystal of <110> ZnTe. The experiment was conducted at room temperature and about 40% relative humidity. The THz-radiation waveforms were sampled with a 15 THz bandwidth and a 23 GHz spectral resolution. The sample was mounted in a galvanometer in the THz-radiation beam and modulated at 10 Hz over a peak-to-peak distance of more than 10 mm. The THz-radiation beam was double-modulated with an optical modulator at 2 kHz and the lock-in amplifier time constant was set to 1 s.

Figure 6:
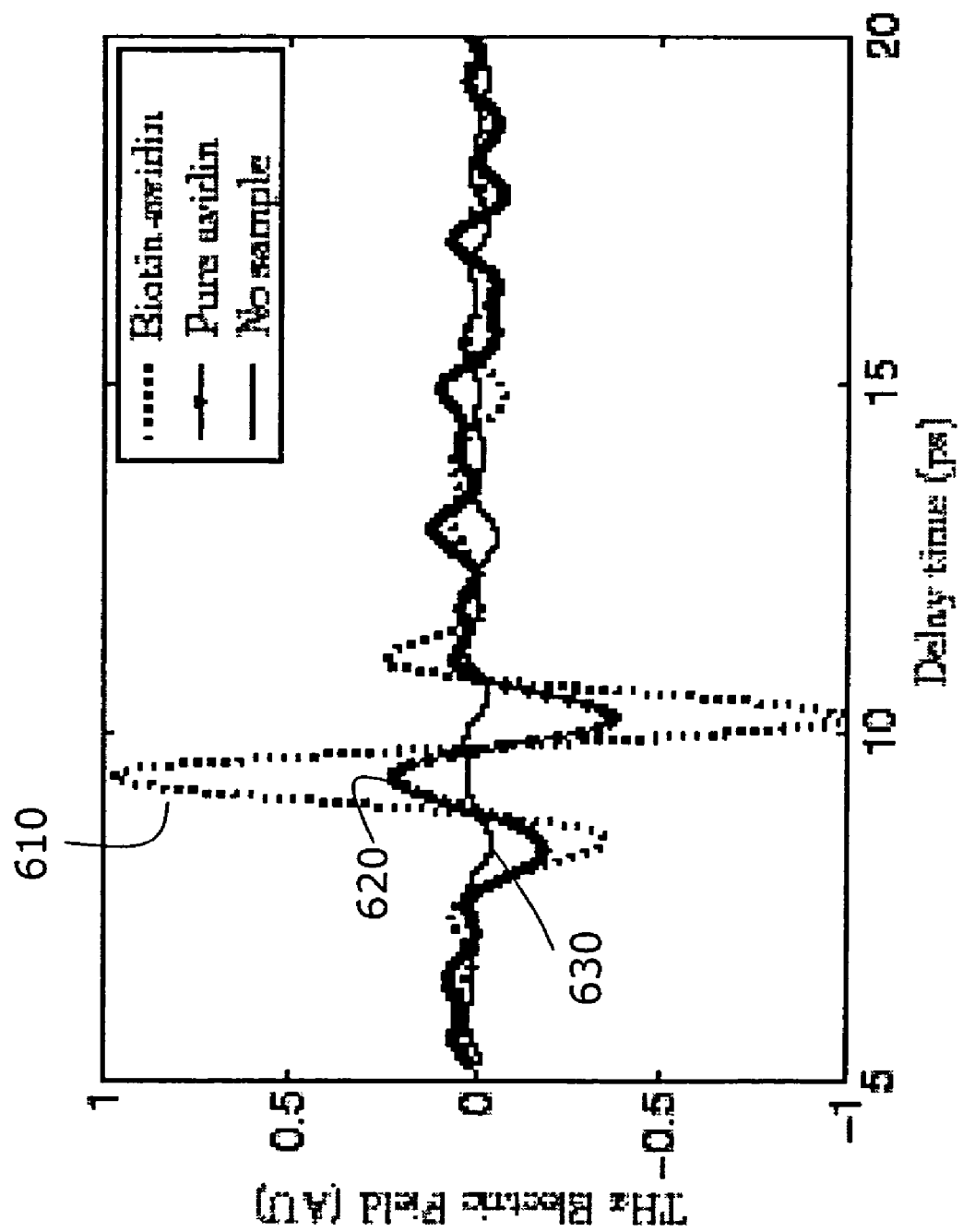
FIG. 6 is a graph of the time domain THz pulses obtained according to the present invention.

The resulting data are shown in FIG. 6. The DTDS of biotin-avidin is shown as a dotted line 610 in FIG. 6. The differences in the THz properties of biotin-avidin and a pure avidin film are apparent from their respective signals. The pure avidin sample is mounted similarly to the biotin-avidin sample. The time-domain DTDS waveform of the pure avidin film is shown as a solid line with a dot 620 in FIG. 6. The avidin only signal 620 is less than half the biotin-avidin signal 610.

Also shown in FIG. 6 is the DTDS of a control with no sample 630. The noise inherent in double-modulated DTDS was measured by completely removing the galvanometric modulator from the THz-radiation beam and monitoring the DTDS signal. Since the beam was no longer being modulated, any measurement was due to noise in the THz-radiation system. The signal from this control experiment is shown as a solid line 630 in FIG. 6.

Example 3

A biotin-coated slide was prepared as in Example 1, and a portion of the slide was exposed to a solution containing avidin conjugated to agarose beads, as illustrated in FIG. 3. Agarose beads 340 bound to several avidin molecules 330 provided a greater change in the index of refraction upon binding to the tethered biotin molecules, thus amplifying the resulting difference signal detected through THz spectroscopy. The signal amplification caused by the agarose beads is apparent in FIG. 4, as the biotin-avidin-agarose signal 420 is approximately 35% greater than the unenhanced biotin-avidin complex.

Example 4

The binding affinity between a tethered molecule on a slide prepared as in Example 1 and a target molecule can be determined by evaluating the degree of binding as a function of concentration of the target molecule. By exposing a slide with a known distribution of tethered molecules to solutions of varying concentration of the target molecule, a relationship between the difference time domain THz spectra and the concentration of the target molecule may be determined.

Figure 5:
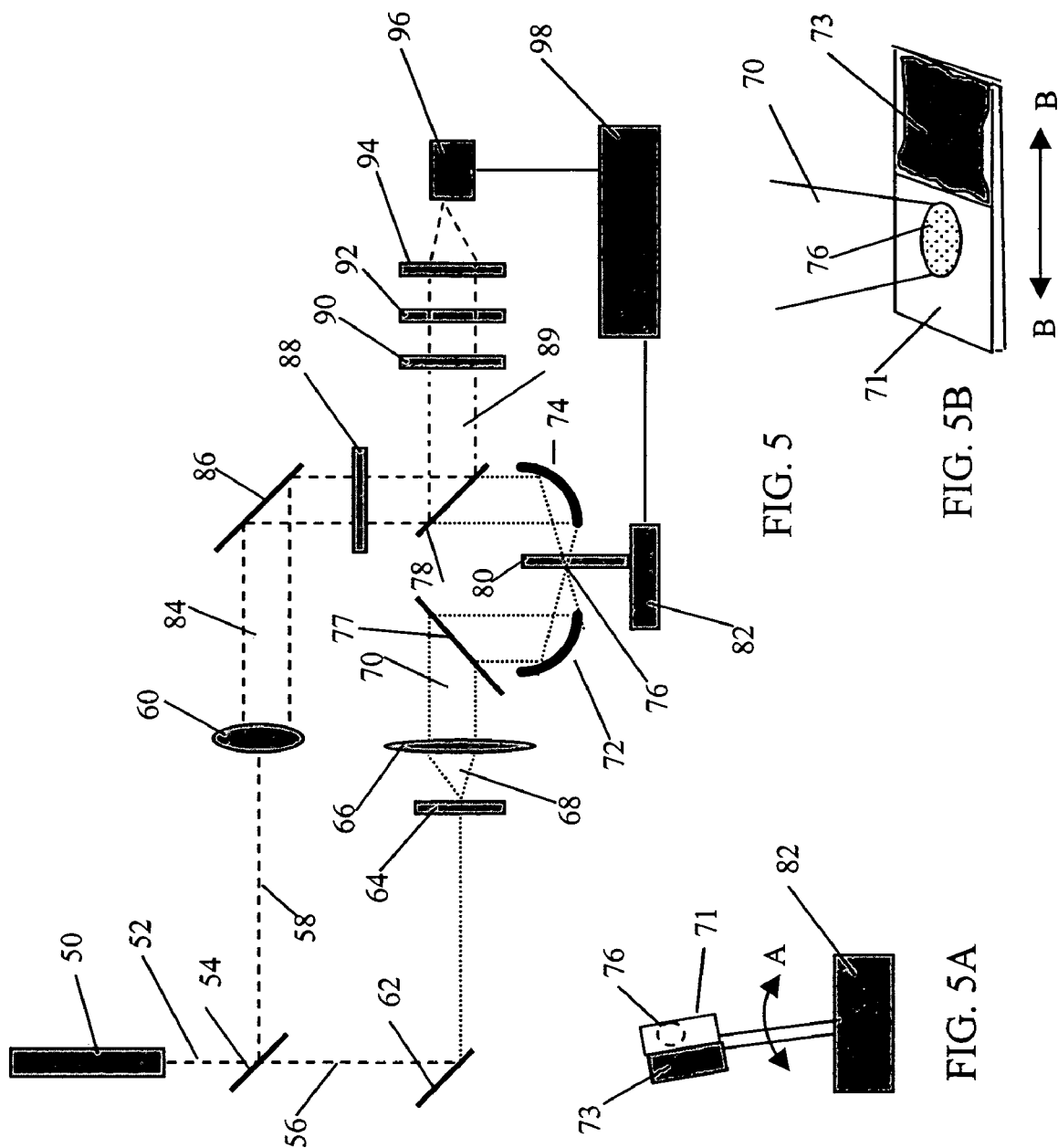
FIG. 5 is a schematic representation of a typical THz apparatus for practicing the present invention.

FIG. 5 shows an apparatus useful for practicing the present invention. The apparatus comprises an optical radiation source 50 which is preferably a laser and associated electronic and optical components for generating femtosecond duration pulses on the order of 10-200 fs at a rate on the order of 70-100 MHz and an average power on the order of 1-2 Watts, preferably about 1.5 W. A Ti:saphire laser emitting radiation with a λ=800 nm and pulse duration of 100 fs at a repetition rate of 82 MHz is preferred, but such preference is not essential to the invention.

The laser radiation travels along path 52 and is split by a beam splitter 54 into a pump beam 56 and a probe beam 58. The pump beam 56 is directed through a reflector 62 onto a THz emitter such as a GaAs semiconductor wafer 64. The emitter produces a pulsed THz beam 68 which is typically expanded and collimated through an optical system 66 into a THz beam 70. Reflective optics 77 and parabolic reflector 72 may be used to direct and focus the THz beam onto a sample located on a sample holder 80. The THz radiation after passing through the sample is next directed onto parabolic and reflective optics 74 and 78, respectively, and then onto a detector 90 which is preferably an electro-optical sampling crystal <110> ZnTe.

The probe beam 58 is also expanded into a beam 84 through optics 60 and directed through a pellicle 86 past a polarizer 88 onto reflective optics 78, so that both the THz radiation beam and the probe beam now travel co-linearly, shown as beam 89, toward the detector 90. A quarter wave plate 92 followed by a Wollaston prism 94 and a detector 96 (which is typically a pair of photodiodes) are used for the balanced detection of the THz radiation, as is described in more detail in S. Mickan, A. Menikh, H. Liu, C. Mannella, R. MacColl, D. Abbott, J. Munch & X.-C. Zhang, "Label-free bioaffinity detection using terahertz technology," in Physics in Medicine and Biology, Vol. 47, No. 21, pp. 3789-96 (November 2002).

The sample holder 80 is shown in better detail in FIG. 5A. In order to practice the present invention, it is important that two readings be taken alternately: one is the reference reading and the second is the target reading. To do this, the sample holder 80 provides an oscillatory motion that oscillates the sample as shown by arrow A so that, in a first position, better shown in FIG. 5B, the focused THz beam 70 illuminates a first area 76 of the sample 71 and, in second position, a second area 73 of the sample 71. It is possible to oscillate the sample with different driving waveforms, depending on the sample geometry. Preferably, a sinusoidal wave is used, although a square wave (or triangle or other waveform) may be preferable in certain circumstances. Detection electronics 98 include synchronizing electronics 82 and may comprise a lock-in amplifier so that readouts are taken only when the focussed beam is solely on the first or the second sample areas.

The high affinity of avidin-biotin complementality demonstrates the above-described biosensor as a strong analytical device for a wide variety of biochemical studies. The biotin-avidin system has broad applications in conjunction with the present invention. Molecules can be tagged with biotin or avidin and then easily detected in minute amounts using the method of this invention. The biotin-avidin system facilitates forming interactions and can be exploited in several applications. Antibodies can be produced for a wide variety of molecules, including proteins, polysaccharides, and nucleic acids as well as more complex particles such as pollens, infectious agents, viruses, and tissue cells. In conjunction with the biotin-avidin system, an amplifying agent, or alone, the present method can detect minute amounts of a wide range of biomolecules.

Although the invention is illustrated and described above with reference to specific embodiments, the invention is not intended to be limited to the details shown. For example, it is within the scope of the present invention to provide the oscillatory motion of the THz spot on the sample, not by moving the sample in and out of a fixed focused position of the THz spot but to oscillate the THz beam laterally between a first and a second position on a fixed sample holder. Similarly, various other modifications may be made in the details within the scope and range of equivalents of the claims and without departing from the invention.

We claim:

1. A method for detecting specific associations between a tethered molecule and an untethered target molecule, the method comprising:
    a) selecting a molecule to serve as the tethered molecule;
    b) alternately impinging THz radiation onto the tethered molecule and onto a sample including a further one of the tethered molecule and the untethered target molecule;
    c) detecting the radiation impinged on the tethered molecule to form a reference signal and the radiation impinged on the sample including the further tethered and target molecules to form a sample signal; and
    d) comparing the reference signal with the sample signal to generate a specimen signal indicative of an association between the selected tethered and target molecules, wherein the target is bound onto a signal amplifying medium.

2. The method according to claim 1 wherein the association is a binding affinity between the selected tethered molecule and the target molecule.

3. The method according to claim 1 wherein the association comprises biomolecular interactions selected from the group consisting of covalent bonds, hybridization interactions, hydrogen bonding interactions, hydrophilic interactions, and specific non-covalent bonds.

4. The method according to claim 1 wherein the tethered molecules comprise molecules selected from the group consisting of ligands, receptors, antigens, antibodies, DNA, and RNA.

5. The method according to claim 1 wherein the target molecules comprise molecules selected from the group consisting of ligands, receptors, antigens, antibodies, DNA, and RNA.

6. The method according to claim 1 wherein the association between the tethered molecule and the target is known and wherein the specimen signal is indicative of the presence of the target in the sample.

7. The method according to claim 1 wherein the amplifying medium is agarose, gold, or carbon.

8. The method according to claim 1 wherein the step of comparing the reference signal with the sample signal comprises subtracting the reference signal from the sample signal.

9. A method for detecting specific associations between a tethered molecule and an untethered target molecule, the method comprising:
    a) selecting a molecule to serve as the tethered molecule;
    b) alternately impinging THz radiation onto the tethered molecule and onto a sample including a further one of the tethered molecule and the untethered target molecule;
    c) detecting the radiation impinged on the tethered molecule to form a reference signal and the radiation impinged on the sample including the further tethered and target molecules to form a sample signal; and
    d) comparing the reference signal with the sample signal to generate a specimen signal indicative of an association between the selected tethered and target molecules, wherein the tethered molecule is biotin and the target molecule is avidin, and the avidin molecule is bound onto agarose beads and the agarose beads serve to amplify the sample signal.

10. The method of claim 1 wherein the sample is secured on a quartz slide.

11. The method according to claim 1 further comprising tethering a molecule to a surface to form the tethered molecule.

12. The method according to claim 1 wherein the target molecule comprises avidin or biotin.

* * * * *